United States Patent
Ichikawa

(10) Patent No.: US 7,651,223 B2
(45) Date of Patent: Jan. 26, 2010

(54) FUNDUS CAMERA

(75) Inventor: Naoki Ichikawa, Okazaki (JP)

(73) Assignee: Nidek Co., Ltd., Gamagori-shi (JP)

( * ) Notice: Subject to any disclaimer, the term of this patent is extended or adjusted under 35 U.S.C. 154(b) by 155 days.

(21) Appl. No.: 12/073,117

(22) Filed: Feb. 29, 2008

(65) Prior Publication Data

US 2008/0212029 A1   Sep. 4, 2008

(30) Foreign Application Priority Data

Mar. 1, 2007   (JP) ............................. 2007-052101

(51) Int. Cl.
*A61B 3/14*   (2006.01)
*A61B 3/10*   (2006.01)

(52) U.S. Cl. .................... 351/208; 351/206; 351/211

(58) Field of Classification Search .......... 351/208–211
See application file for complete search history.

(56) References Cited

U.S. PATENT DOCUMENTS

| | | | | |
|---|---|---|---|---|
| 4,712,894 A | * | 12/1987 | Nunokawa | .................. 351/208 |
| 5,463,430 A | | 10/1995 | Isogai et al. | |
| 2001/0024265 A1 | * | 9/2001 | Fujieda | .................. 351/208 |
| 2009/0128778 A1 | * | 5/2009 | Honda et al. | .................. 351/245 |

FOREIGN PATENT DOCUMENTS

| | | |
|---|---|---|
| EP | 1 452 128 A1 | 9/2004 |
| EP | 1 535 566 A1 | 6/2005 |
| EP | 1 864 609 A1 | 12/2007 |
| JP | A-06-046999 | 2/1994 |
| JP | A-11-004808 | 1/1999 |
| JP | A-2004-290535 | 10/2004 |
| JP | A-2007-202724 | 8/2007 |
| WO | WO 00/30528 | 6/2000 |
| WO | WO 2006/106977 A1 | 10/2006 |

* cited by examiner

*Primary Examiner*—Jordan M. Schwartz
(74) *Attorney, Agent, or Firm*—Oliff & Berridge, PLC

(57) ABSTRACT

A fundus camera capable of preferably photographing the periphery of a fundus irrespective of the state of an eye includes a photographing optical system having a photographing optical axis for photographing the fundus, a fundus observation optical system for picking up a fundus observation image, an alignment target projection optical system for projecting an alignment target onto an anterior segment of the eye, an alignment target image detection optical system, a photographing unit housing the systems, a moving mechanism moving the unit for alignment of the axis, a fixation target presenting system for guiding a visual line direction, a target presenting position being selectable or changeable, a display unit, and a controller controlling the display unit to display the observation and target images, wherein the controller includes a program for forming and displaying a reticle mark in displaying the observation image varying the shape of the mark with the presenting position.

9 Claims, 7 Drawing Sheets

FUNDUS CAMERA

BACKGROUND OF THE INVENTION

1. Field of the Invention

The present invention relates to a fundus camera which photographs a fundus of an examinee's eye.

2. Description of Related Art

There is known a fundus camera which changes a display position of a reticle mark that defines an alignment reference in accordance with a presenting position of a fixation target on which an examinee's eye is fixated (see Japanese Patent Application Unexamined Publication Hei11-4808). In such an apparatus, especially in photographing the periphery of a fundus of the eye, the display position of the reticle mark is changed so that a photographing optical axis of the fundus camera is aligned with the pupil center in accordance with the presenting position of the fixation target in order to prevent fundus illumination light from being blocked by an iris of the eye.

However, in the photographing of the periphery of the fundus, it is not necessarily most appropriate to perform the alignment of the photographing optical axis with respect to the pupil center. This is because if, for example, the photographing optical axis is largely deviated from a corneal vertex in the photographing, a photographing image of the fundus is apt to suffer flares. Accordingly, the alignment reference position such that a preferable photographing image of the fundus can be obtained differs with a pupil diameter, a corneal shape or other factors of the eye.

SUMMARY OF THE INVENTION

An object of the invention is to overcome the problems described above and to provide a fundus camera which is capable of preferably performing photographing of the periphery of a fundus of an examinee's eye irrespective of the state of the eye.

To achieve the objects and in accordance with the purpose of the present invention, a fundus camera comprises a photographing optical system having a photographing optical axis, for photographing a fundus of an examinee's eye, a fundus observation optical system having an image-pickup element which picks up an observation image of the fundus of the eye, an alignment target projection optical system for projecting an alignment target onto an anterior segment of the eye, an alignment target image detection optical system having a photodetector which detects an image of the alignment target, a photographing unit which houses the photographing optical system, the fundus observation optical system, the alignment target projection optical system and the alignment target image detection optical system, a moving mechanism which moves the photographing unit in order to perform alignment of the photographing optical axis so as to have a predetermined positional relationship with the eye, a fixation target presenting system for presenting a fixation target for guiding a direction of a visual line of the eye, a presenting position of the fixation target being arranged to be selectable or changeable, a display unit, and a controller which controls the display unit to display the fundus observation image and the alignment target image on a screen of the display unit, wherein the controller includes a program for electrically forming and displaying a reticle mark that defines an alignment reference in a predetermined position on the screen at the time of displaying the fundus observation image while varying a display shape of the reticle mark in accordance with the presenting position of the fixation target.

In another aspect of the present invention, a fundus camera comprises a photographing optical system having a photographing optical axis, for photographing a fundus of an examinee's eye, a fundus observation optical system having a first image-pickup element which picks up an observation image of the fundus of the eye, an alignment target projection optical system for projecting an alignment target onto an anterior segment of the eye, an anterior-segment observation optical system having a second image-pickup element which picks up an observation image of the anterior segment of the eye and an image of the alignment target, a photographing unit which houses the photographing optical system, the fundus observation optical system, the alignment target projection optical system and the anterior-segment observation optical system, a moving mechanism which moves the photographing unit in order to perform alignment of the photographing optical axis so as to have a predetermined positional relationship with the eye, a fixation target presenting system for presenting a fixation target for guiding a direction of a visual line of the eye, a presenting position of the fixation target being arranged to be selectable or changeable, a display unit, and a controller which controls the display unit to switch display on a screen of the display unit between the fundus observation image and the alignment target image, and the anterior-segment observation image and the alignment target image, wherein the controller includes a program for electrically forming and displaying a reticle mark that defines an alignment reference in a predetermined position on the screen at least one of at the time of displaying the fundus observation image and at the time of displaying the anterior-segment observation image while varying a display shape of the reticle mark in accordance with the presenting position of the fixation target.

Additional objects and advantages of the invention are set forth in the description which follows, are obvious from the description, or may be learned by practicing the invention. The objects and advantages of the invention may be realized and attained by the fundus camera in the claims.

BRIEF DESCRIPTION OF THE DRAWINGS

The accompanying drawings, which are incorporated in and constitute apart of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
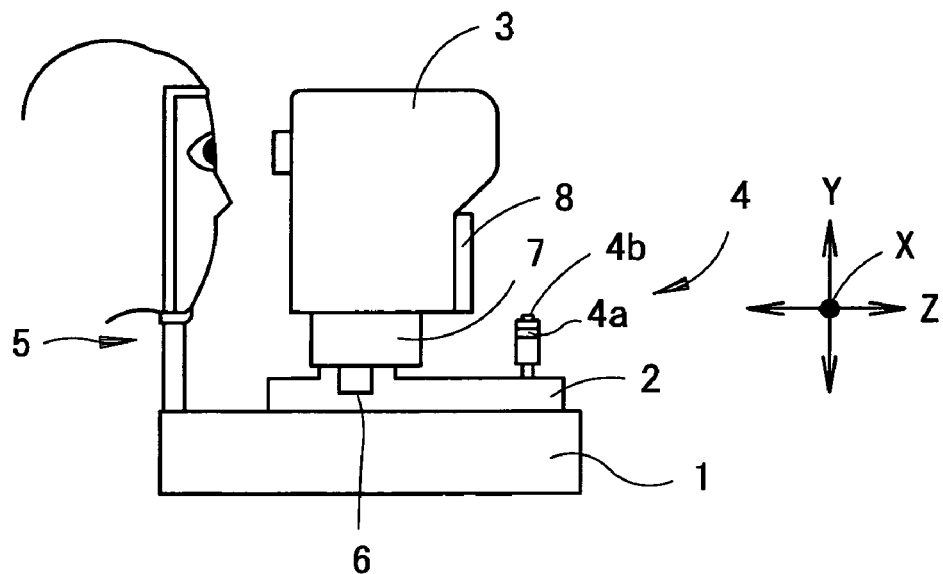
FIG. 1 is a view showing a schematic configuration of a fundus camera according to a preferred embodiment of the present invention.

A detailed description of a fundus camera according to preferred embodiments of the present invention is provided below with reference to the accompanying drawings. FIG. 1 is a view showing a schematic configuration of a fundus camera according to a preferred embodiment of the present invention.

The fundus camera comprises a base 1, a mobile base 2 movable in a right/left direction (hereinafter referred to as an "X-direction") and a back/forth direction (hereinafter referred to as a "Z-direction") with reference to the base 1 through tilting operation of a joystick 4, a photographing unit 3 movable in the right/left direction, an up/down direction (hereinafter referred to as a "Y-direction"), and the back/forth direction with reference to the mobile base 2 under control of a controller 80 to be described later, and a face support unit 5 fixedly provided on the base 1 for supporting a face (a head) of an examinee. Moving units 6 and 7 include a Y table movable in the Y-direction, a Z table movable in the Z-direction which is placed on the Y table, and an X table movable in the X-direction which is placed on the Z table, and the photographing unit 3 is placed on the X table. The moving unit 7 moves the X and Z tables individually by a motor and other moving mechanisms so as to move the photographing unit 3 in the X-direction and/or the Y-direction. The moving unit 6 moves the Y table by a motor and other moving mechanisms so as to move the photographing unit 3 in the Y-direction. Besides, for the moving mechanisms as the moving units 6 and 7, a known mechanism may be used. In addition, the photographing unit 3 is moved in the Y-direction also by driving of the moving unit 6 through rotational operation of a rotating knob 4a of the joystick 4. A monitor (a display) 8 which displays images including an observation image of an anterior segment of an examinee's eye, an observation image of a fundus of the eye, and a photographing image of the fundus is provided on the examiner's side of the photographing unit 3.

Figure 2:
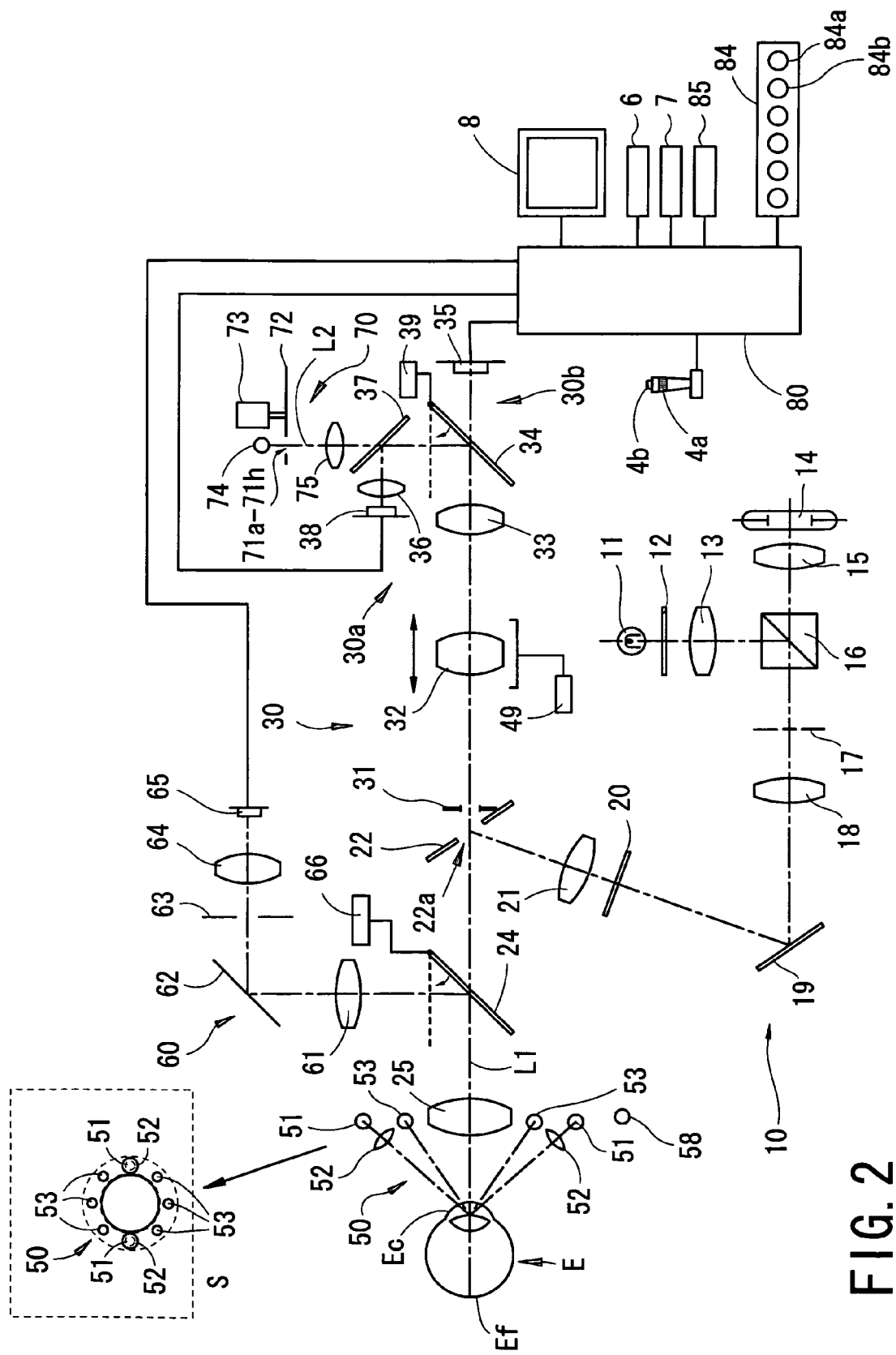
FIG. 2 is a view showing a schematic configuration of an optical system and a control system of the fundus camera.

FIG. 2 is a view showing a schematic configuration of an optical system and a control system housed in the photographing unit 3. The optical system comprises an illumination optical system 10, a fundus observation/photographing optical system 30, an alignment target projection optical system 50, an anterior-segment observation optical system 60 and a fixation target presenting optical system 70.

<Illumination Optical System 10>

The illumination optical system 10 comprises an illumination optical system for fundus observation and an illumination optical system for photographing. Illumination light emitted from an illumination light source 11 for fundus observation such as a halogen light is made into infrared illumination light by an infrared transmission filter 12 which transmits infrared light with a wavelength of less than about 900 nm, and is reflected by a dichroic mirror 16 via a condenser lens 13. The dichroic mirror 16 has a wavelength-selecting property of reflecting infrared light and transmitting visible light. The infrared illumination light reflected by the dichroic mirror 16 passes through a ring slit plate 17, a relay lens 18, a total reflection mirror 19, a black dot plate 20 having a black dot at its center and a relay lens 21, and is reflected by an apertured mirror 22 and is projected on to a fundus Ef of an examinee's eye E via an objective lens 25. Besides, an infrared light source such as an infrared light-emitting diode may be used instead of the light source 11 such as the halogen light and the infrared transmission filter 12.

Visible illumination light emitted from a visible illumination light source 14 for photographing such as a flash light passes through a condenser lens 15 and is transmitted through the dichroic mirror 16 and is projected onto the fundus Ef via the ring slit plate 17 to the objective lens 25.

<Fundus Observation/Photographing Optical System 30>

The fundus observation/photographing optical system 30 comprises a fundus observation optical system 30a and a photographing optical system 30b. The infrared light and the visible light reflected from the fundus Ef pass through the objective lens 25, an aperture 22a in the apertured mirror 22, a photographing diaphragm 31 placed in the vicinity of the aperture 22a and a focusing lens 32 and enter an image forming lens 33. The photographing diaphragm 31 is placed in a position substantially conjugate with a pupil of the eye E with reference to the objective lens 25. The focusing lens 32 is placed so as to be movable by a moving unit 49 consisting of a moving mechanism such as a motor in a direction of an optical axis L1 of the fundus observation/photographing optical system 30 (the objective lens 25). A movable total reflection mirror 34 is placed so as to be insertable into/removable from an optical path of the fundus observation/photographing optical system 30 by an inserting/removing unit 39 consisting of an inserting/removing mechanism such as a motor, and is removed from the optical path at the time of photographing. When the mirror 34 is removed from the optical path, the visible reflection light is photo-received on a CCD camera (an image-pickup element) 35 for photographing having sensitivity to a visible range and forms an image of the fundus Ef (a fundus photographing image). Meanwhile, when the mirror 34 is inserted into the optical path, the infrared reflection light reflected by the mirror 34 is reflected by a dichroic mirror 37, is photo-received on a CCD camera (an image-pickup element) 38 for fundus observation having sensitivity to an infrared range via a relay lens 36 and forms an image of the fundus Ef (a fundus observation image). The dichroic mirror 37 has a wavelength-selecting property of reflecting infrared light and transmitting visible light.

A movable dichroic mirror 24 that defines an optical path dividing member is placed so as to be insertable into/removable from an optical path between the objective lens 25 and the apertured mirror 22 (the photographing diaphragm 31) by an inserting/removing unit 66 consisting of an inserting/removing mechanism such as a motor, and is removed from the optical path at the time of photographing. The dichroic mirror 24 has a wavelength-selecting property of reflecting infrared light with a wavelength of about 900 nm or more from an infrared illumination light source 58 for anterior-segment observation and the alignment target projection optical system 50 to be described later, and transmitting the infrared light with the wavelength of less than about 900 nm from the illumination optical system for fundus observation.

<Alignment Target Projection Optical System 50>

As shown in a figure S enclosed with dashed lines in FIG. 2, the alignment target projection optical system 50 comprises two first projection optical systems in a pair which have optical axes placed so as to be laterally symmetrical with respect to the optical axis L1, and six second projection optical systems in pairs which have optical axes placed so as to be laterally symmetrical with respect to the optical axis L1. Each of the two first projection optical systems includes an infrared light source 51 such as an infrared light-emitting diode which emits the infrared light with the wavelength of about 900 nm or more and a collimating lens 52 and projects infrared target light at an infinite distance (projects an alignment target at an infinite distance) onto an anterior segment (a cornea Ec) of the eye E with substantially parallel light. Meanwhile, each of the six second projection optical systems includes an infrared light source 53 such as an infrared light-emitting diode which emits the infrared light with the wavelength of about 900 nm or more, and projects infrared target light at a finite distance (projects an alignment target at a finite distance) onto the anterior segment (the cornea Ec) of the eye E with divergent light. Besides, in the preferred embodiment of the present invention, as shown in the figure S enclosed with the dashed lines in FIG. 2, the first projection optical systems and the second projection optical systems are placed at intervals of 45° each other on a concentric circle having the optical axis L1 as its center (e.g., a concentric circle of 3-mm radius).

<Anterior-Segment Observation Optical System 60>

Infrared illumination light emitted from the infrared illumination light source 58 for anterior-segment observation such as an infrared light-emitting diode which emits the infrared light with the wavelength of about 900 nm or more is reflected by the anterior segment of the eye E and the dichroic mirror 24 inserted into the optical path, is photo-received on a CCD camera (an image-pickup element) 65 for anterior-segment observation having sensitivity to an infrared range via a field lens 61, a total reflection mirror 62, a diaphragm 63 and a relay lens 64, and forms an image of the anterior segment of the eye E (an anterior-segment observation image). The CCD camera 65 doubles as image-pickup means for alignment target image detection (i.e., the anterior-segment observation optical system 60 doubles as an alignment target image detection optical system), and picks up the anterior-segment image formed by the light source 58 and images of the alignment targets formed by the alignment target projection optical system 50.

<Fixation Target Presenting Optical System 70>

Figure 3:
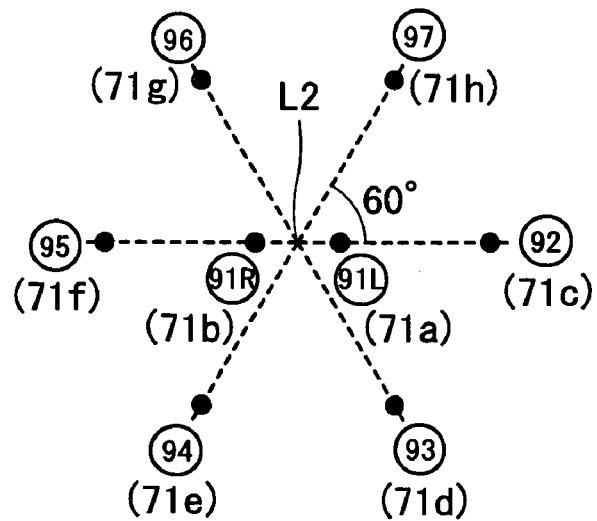
FIG. 3 is a view illustrating presenting positions of a fixation target.

Red fixation target light emitted from a fixation target light source (a fixation lamp) 74 such as a red light-emitting diode passes through an aperture in a shielding plate 72 and a relay lens 75 and is transmitted through the dichroic mirror 37. The red fixation target light transmitted through the dichroic mirror 37 is reflected by the dichroic mirror 34 inserted into the optical path, passes through the image forming lens 33 to the objective lens 25, and is projected onto the fundus Ef (i.e., a fixation target is projected there onto). The shielding plate 72 has apertures 71a to 71h, one of which is placed in such a position in front of the light source 74 that is not on an optical axis L2 coaxial with the optical axis L1 by being rotated by a motor 73. As shown in FIG. 3, one of eight fixation target presenting positions is selected by selecting one of the apertures 71a to 71h. A fixation target presenting position 91L (a standard position in photographing the left eye) corresponding to the aperture 71a is selected when photographing the vicinity of a posterior pole area (a center portion) of the fundus of the left eye which includes a macular spot and an optic papilla in a balanced manner so as to be the center of the image. Meanwhile, a fixation target presenting position 91R (a standard position in photographing the right eye) corresponding to the aperture 71b is selected when photographing the vicinity of a posterior pole area (a center portion) of the fundus of the right eye including a macular spot and an optic papilla in a balanced manner so as to be the center of the image. In addition, fixation target presenting positions 92 to 97 corresponding to the apertures 71c to 71h are selected when photographing peripheral areas (peripheral portions) of the fundus.

Figure 4A:
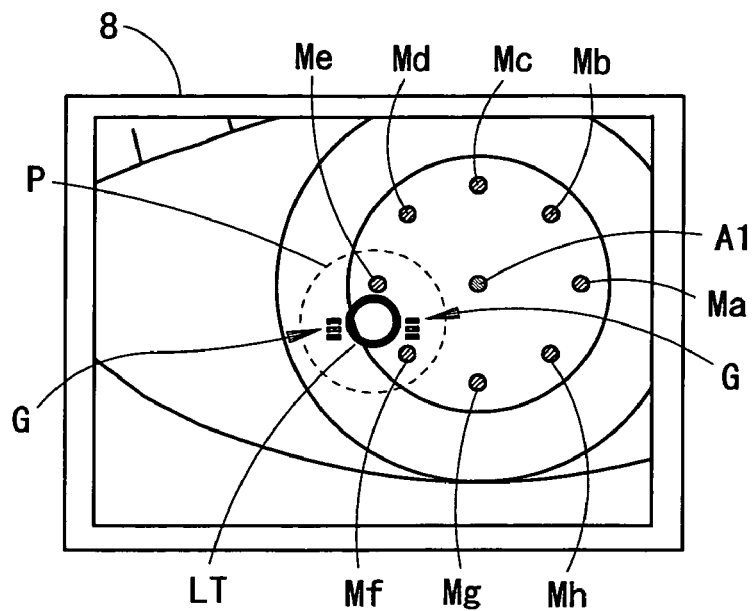
FIGS. 4A and 4B are views showing examples in displaying an observation image of an anterior segment of an examinee's eye.
Figure 4B:
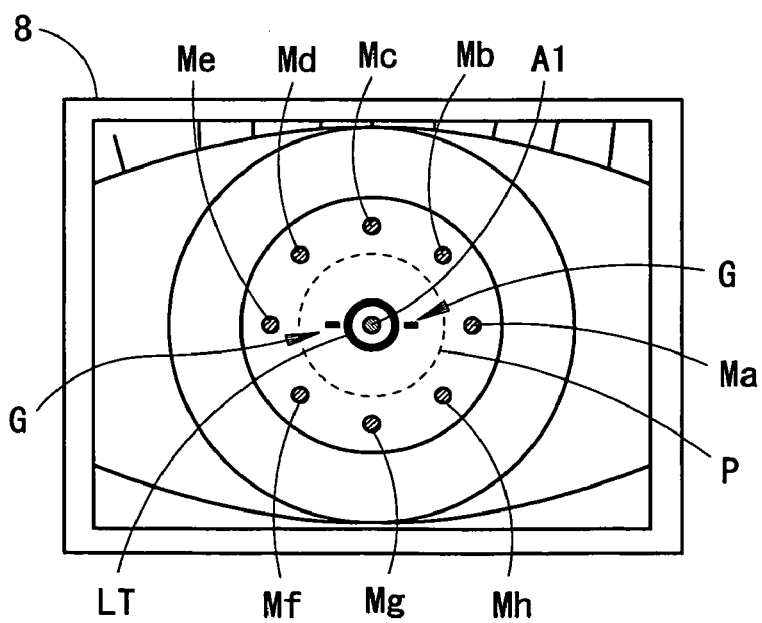

Image signals outputted from the CCD cameras 65, 38 and 35 are inputted to the controller 80. The controller 80 detects the alignment target images based on the image signal from the CCD camera 65 and obtains an alignment deviation amount of the optical axis L1 (the photographing unit 3) with respect to the eye E in the X- and Y-directions. In addition, the controller 80 is connected to the monitor 8 and performs a display control of the monitor 8. For example, both at the time of displaying the anterior-segment observation image by the CCD camera 65 (see FIGS. 4A and 4B) and at the time of displaying the fundus observation image by the CCD camera 38 (see FIGS. 5A and 5B), the controller 80 controls to electrically form and display a reticle mark LT that defines an alignment reference in a predetermined position on a screen of the monitor 8 while controlling to electrically form and display on the screen of the monitor 8 an alignment mark A1 of which a relative distance from the reticle mark LT varies in accordance with the alignment deviation amount in the X- and Y-directions obtained based on the image signal from the CCD camera 65. The controller 80 is connected with the moving units 6, 7 and 49, the inserting/removing units 39 and 66, the rotation knob 4a, a photographing switch 4b, a switch unit 84 including various switches, a memory 85, the light sources, and other constituent elements (in FIG. 2, apart of connection lines are not shown). The switch unit 84 includes a focusing switch 84a, a fixation target presenting position changing switch 84b and other switches.

Operation of the fundus camera having the above-described configuration in the case of photographing the center portion of the fundus (hereinafter, referred to as standard photographing) and operation of the fundus camera having the above-described configuration in the case of photographing the peripheral portion of the fundus (hereinafter, referred to as periphery photographing) will be described separately. Provided below is a description in the case of photographing the right eye.

A description in the case of the standard photographing is provided. First, the face of the examinee is supported by the face support unit 5. In addition, the fixation target presenting position 91R shown in FIG. 3 is selected through operation of the switch 84b. In the initial stage, the dichroic mirror 24 has been already inserted into the optical path, and the anterior-segment observation image picked up by the CCD camera 65 is displayed (appears) on the monitor 8. The controller 80 controls to electrically form and display in the center of the screen of the monitor 8 the reticle mark LT and a circular mark P indicating the minimum pupil diameter of photographing. The photographing unit 3 is moved in the X-direction and/or the Y-direction so that the anterior-segment observation image is placed in the center of the screen of the monitor 8. In addition, the photographing unit 3 is moved in the Z-direction so that the anterior-segment observation image is brought into focus. When the anterior-segment observation image comes to be placed in the vicinity of the center of the screen of the monitor 8, eight alignment target images Ma to Mh formed by the alignment target projection optical system 50 also come to be displayed (appear)(see FIG. 4A). The reticle mark LT used for standard photographing is set to have a display shape and a display position so that the optical axis L1 is positioned in the vicinity of a corneal vertex of the eye E and the vicinity of a pupil center of the eye E (i.e., alignment of the optical axis L1 is performed) when the alignment mark A1 is positioned within (enters) the reticle mark LT.

When the alignment target images Ma to Mh are picked up by the CCD camera 65, the controller 80 obtains the alignment deviation amount in the X- and Y-directions based on the image signal from the CCD camera 65. In the preferred embodiment of the present invention, the controller 80 detects a center position of the alignment target images Ma to Mh in the X- and Y-directions as a substantial corneal center, and calculates a difference (a deviation amount) between the center position and an alignment reference position in the X- and Y-directions previously set in the CCD camera 65 (e.g., an intersection point of an image-pickup surface of the CCD camera 65 and the optical axis L1).

When the center position of the alignment target images Ma to Mh is obtained, the controller 80 controls to electrically form and display the alignment mark A1 in a position on the monitor 8 which corresponds to the center position. In addition, the controller 80 controls display of the alignment mark A so that the relative distance from the reticle mark LT displayed on the monitor 8 varies in accordance with the alignment deviation amount in the X- and Y-directions obtained based on the image signal from the CCD camera 65. Besides, a program for performing the display control of the monitor 8 based on relationships between the alignment deviation amounts in the X- and Y-directions and the relative distances of the alignment mark A1 from the reticle mark LT at the time of displaying the anterior-segment observation image and at the time of displaying the fundus observation image is previously stored in the memory 85, and the controller 80 performs the display control of the monitor 8 by using the program.

When the alignment deviation amount in the X- and Y-directions changes by the movement of the photographing unit 3 with respect to the eye E in the X- and Y-directions, the controller 80 controls to change the relative distance of the alignment mark A1 from the reticle mark LT. That is to say, a display position (a formation position) of the alignment mark A1 with respect to the reticle mark L1 varies in accordance with the change in the alignment deviation amount in the X- and Y-directions.

The photographing unit 3 is further moved in the X- and Y-directions so that the alignment mark A1 is displayed within the reticle mark LT (see FIG. 4B), and the alignment of the optical axis L1 (the photographing unit 3) with respect to the eye E in the X- and Y-directions is performed. In addition, it is checked whether or not the pupil diameter of the eye E is bigger than the circular mark P indicating the minimum pupil diameter.

In addition, the controller 80 compares an interval between the images of the infinite alignment targets with intervals between the images of the finite alignment targets, and obtains an alignment deviation amount of the photographing unit 3 with respect to the eye E in the Z-direction (see U.S. Pat. No. 5,463,430 corresponding to Japanese Patent Application Unexamined Publication No. Hei06-46999). Then, the controller 80 increases/decreases the number of indicators G based on the alignment deviation amount in the Z-direction which is obtained based on the image signal from the CCD camera 65. Then, the photographing unit 3 is moved in the Z-direction so that only one indicator G is displayed (see FIG. 4B), and alignment of the photographing unit 3 with respect to the eye E in the Z-direction is performed.

The controller 80 judges whether or not the alignment in the X- and Y-directions is performed appropriately by determining whether or not the alignment deviation amount in the X- and Y-directions stays within a predetermined range of alignment completion for a given period of time. In addition, the controller 80 judges whether or not the alignment in the Z-direction is performed appropriately by determining whether or not the alignment deviation amount in the Z-direction stays within a predetermined range of alignment completion for a given period of time.

When the alignment states in the X-, Y- and Z-directions satisfy predetermined conditions for alignment completion, the controller 80 automatically switches the display on the monitor 8 from the anterior-segment observation image to the fundus observation image. Besides, instead of the automatic display switching being performed, a message for manual display switching may be informed (displayed).

Figure 5A:
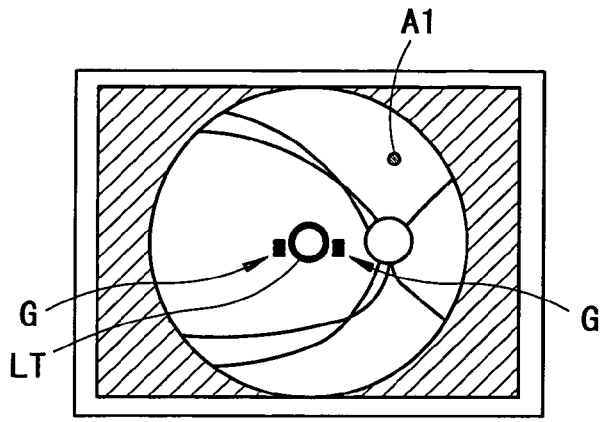
FIGS. 5A and 5B are views showing examples in displaying an observation image of a fundus of the eye.
Figure 5B:
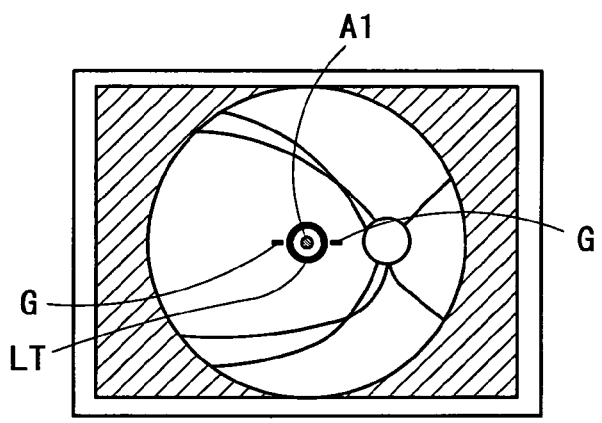

At the time of displaying the fundus observation image, the controller 80, similarly to the case of displaying the anterior-segment observation image, controls to electrically form and display the reticle mark LT in a predetermined position on the screen of the monitor 8 while controlling to electrically form and display on the screen of the monitor 8 the alignment mark A1 of which the relative distance from the reticle mark LT varies in accordance with the alignment deviation amount in the X- and Y-directions (see FIG. 5A).

In addition, the controller 80 controls the display position of the alignment mark A1 so that the relative distance from the reticle mark LT corresponding to the alignment deviation amount in the X- and Y-directions at the time of displaying the fundus observation image differs from that at the time of displaying the anterior-segment observation image. To be more specific, the controller 80 controls the display of the alignment mark A1 so that the relative distance from the reticle mark LT in accordance with the alignment deviation amount in the X- and Y-directions at the time of displaying the fundus observation image becomes longer (e.g., about four or five times) than that at the time of displaying the anterior-segment observation image. That is to say, the controller 80 controls the display of the alignment mark A1 so that a proportion of change in the relative distance from the reticle mark LT with respect to a proportion of change in the alignment deviation amount in the X- and Y-directions at the time of displaying the fundus observation image becomes larger than that at the time of displaying the anterior-segment observation image.

In addition, also in the Z-direction, the controller 80 increases/decreases the number of indicators G based on the alignment deviation amount in the Z-direction similarly to the case of displaying the anterior-segment observation image. In this case, similarly to the case of the alignment in the X- and Y-directions, display of the indicators G (e.g., the number of the indicators G) varying in accordance with the alignment deviation amount in the Z-direction at the time of displaying the fundus observation image may differ from that at the time of displaying the anterior-segment observation image. The photographing unit 3 is moved in the X- and Y-directions so that the alignment mark A1 is displayed within the reticle mark LT (see FIG. 5B) and the alignment of the optical axis L1 (the photographing unit 3) with respect to the eye E in the X- and Y-directions is performed. In addition, the photographing unit 3 is moved in the Z-direction so that only one indicator G is displayed (see FIG. 5B), and the alignment of the photographing unit 3 with respect to the eye E in the Z-direction is performed. Besides, in a case where the alignment of the optical axis L1 with respect to the eye E deviates widely, the display on the monitor 8 is automatically switched from the fundus observation image to the anterior-segment observation image. Also at this time, a message for the manual display switching may be informed (displayed) instead of the automatic display switching being performed.

Next, focusing is performed through operation of the switch 84a while the fundus observation image on the monitor 8 is observed. The controller 80 drives the moving unit 49 and moves the focusing lens 32 based on an input signal by the switch 84a. Then, when a desired area in the fundus Ef becomes preferably observable, photographing is performed through operation of the switch 4b. The controller 80 drives the inserting/removing unit 39 so as to remove the mirror 34 from the optical path, drives the inserting/removing unit 66 so as to remove the dichroic mirror 24 from the optical path, and lights the light source 14. The fundus photographing image picked up by the CCD camera 35 is stored in the memory 85 and displayed on the monitor 8.

Figure 6A:
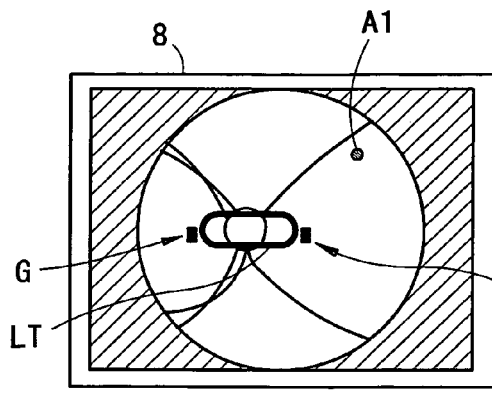
FIGS. 6A, 6B and 6C are views showing a display shape of a reticle mark varied in accordance with the presenting positions of the fixation target.
Figure 6B:
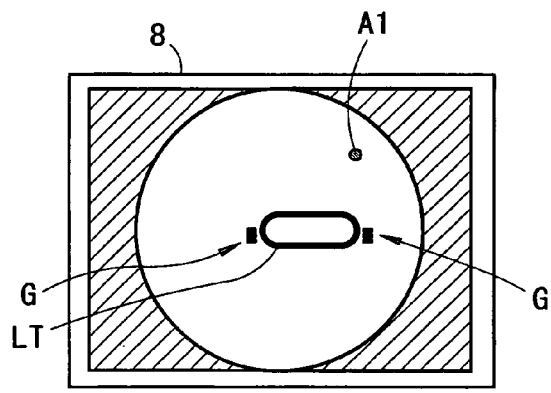
Figure 6C:
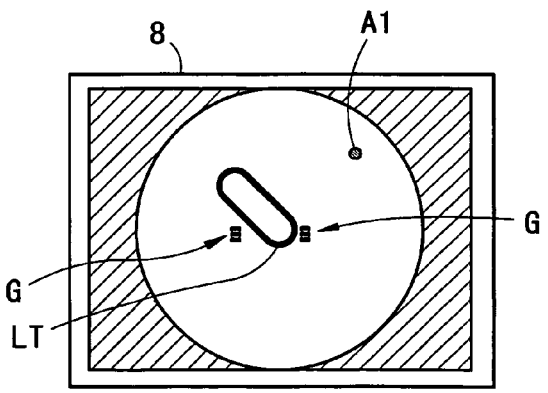

A description in the case of the periphery photographing is provided. When the presenting position of the fixation target is changed from the position for standard photographing to the position for periphery photographing (when the position for periphery photographing is selected) through operation of the switch 84b, the controller 80 varies a display shape of the reticle mark LT in accordance with the changed (selected) presenting position of the fixation target. In the periphery photographing, eccentricities of the corneal vertex and the pupil center of the eye E become larger with an amount (angle) of inclination in a direction of a visual line of the eye E. The controller 80 varies the display shape of the reticle mark LT in accordance with the changed (selected) presenting position of the fixation target so that when the alignment mark A1 is displayed within the reticle mark LT, the alignment of the optical axis L1 is performed so that the optical axis L1 falls within a predetermined region from the vicinity of the corneal vertex to the vicinity of the pupil center of the eye E (on a virtual line between the corneal vertex and the pupil center). In other words, when the reticle mark LT is used for periphery photographing, it is set to have a display shape such that when the alignment mark A1 is placed within the reticle mark LT, the optical axis L1 is placed within the predetermined region from the vicinity of the corneal vertex to the vicinity of the pupil center of the eye E. For example, when the fixation target presenting position 95 in FIG. 3 is selected, the display shape of the reticle mark LT is varied to the one shown in FIG. 6A. When the fixation target presenting position 92 in FIG. 3 is selected, the display shape of the reticle mark LT is varied to the one shown in FIG. 6B. When the fixation target presenting position 94 in FIG. 3 is selected, the display shape of the reticle mark LT is varied to the one shown in FIG. 6C. Besides, as the amount (angle) of the inclination in the direction of the visual line of the eye E becomes larger, an eccentricity of the reticle mark LT at the time of the periphery photographing becomes larger than that of the reticle mark LT at the time of the standard photographing.

Incidentally, a program for controlling the display of the monitor 8 based on a relationship between the presenting position of the fixation target and the display shape of the reticle mark LT varied in accordance with the presenting position of the fixation target is previously stored in the memory 85, and the controller 80 controls the display of the monitor 8 by using the program. That is to say, the display shapes of the reticle mark LT in all the presenting positions are set based on a virtual line between a display position of the alignment mark A1 at the time when the alignment of the optical axis L1 is performed with respect to the vicinity of the corneal vertex and a display position of the alignment mark A1 at the time when the alignment of the optical axis L1 is performed with respect to the vicinity of the pupil center, and are stored in the memory 85. The reticle mark LT may have the display shape of a frame which surrounds the virtual line or a line which traces the virtual line. In the preferred embodiment of the present invention, the reticle mark LT is set to have the display shape of a frame so that a permissible range of the alignment covers up to the position of the optical axis L1 deviated by 0.5 mm from the virtual line.

Figure 7A:
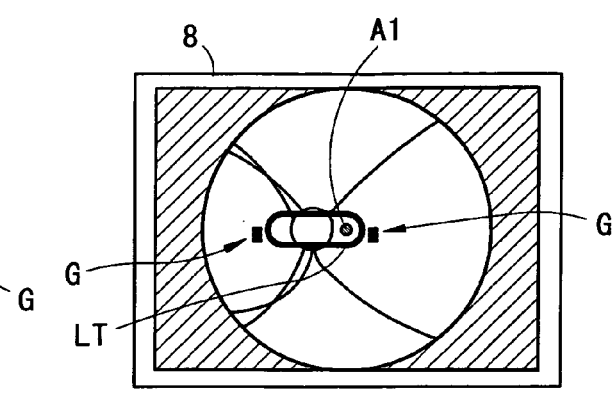
FIGS. 7A, 7B and 7C are views showing examples in displaying the fundus observation image at the time of photographing the periphery of the fundus such that a papilla of the right eye is arranged to be the center of the image.
Figure 7B:
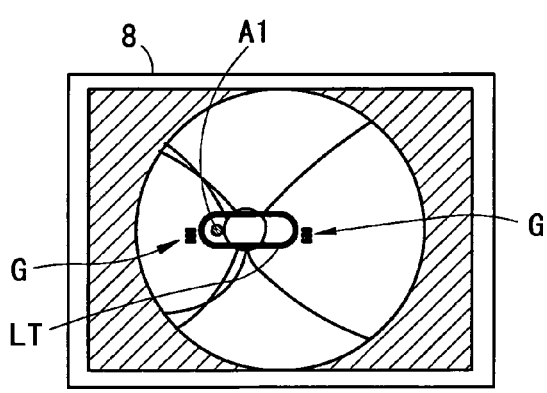
Figure 7C:
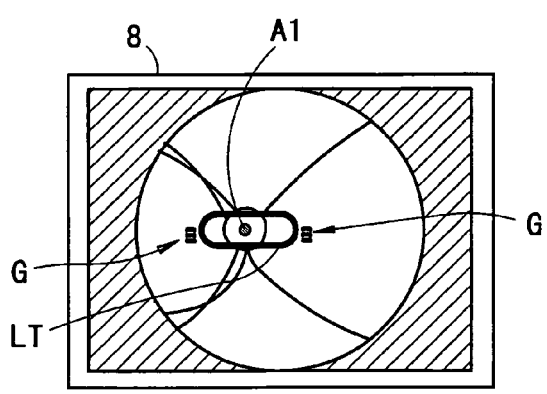

The periphery photographing in a case where the fixation target presenting position 95 in FIG. 3 is selected (periphery photographing such that the optic papilla of the right eye is arranged to be the center of the image) is described. In this case, the direction of the visual line of the eye E is leftward when seen from the examinee (see FIGS. 8A to 8C). The controller 80 controls to form and display the reticle mark LT for periphery photographing having the display shape extending leftward (see FIGS. 7A to 7C) with respect to the display shape of the reticle mark LT for standard photographing (see FIGS. 5A and 5B). In other words, the controller 80 controls to display the reticle mark LT for periphery photographing having the display shape which is made larger in a direction where the direction of the visual line of the eye E is guided than the display shape of the reticle mark LT for standard photographing.

Figure 8A:
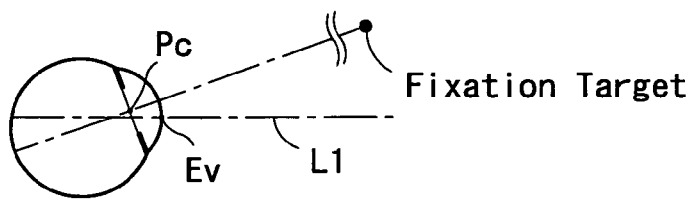
FIGS. 8A, 8B and 8C are views showing a relationship between the eye of which a direction of a visual line is leftward and a photographing optical axis.
Figure 9A:
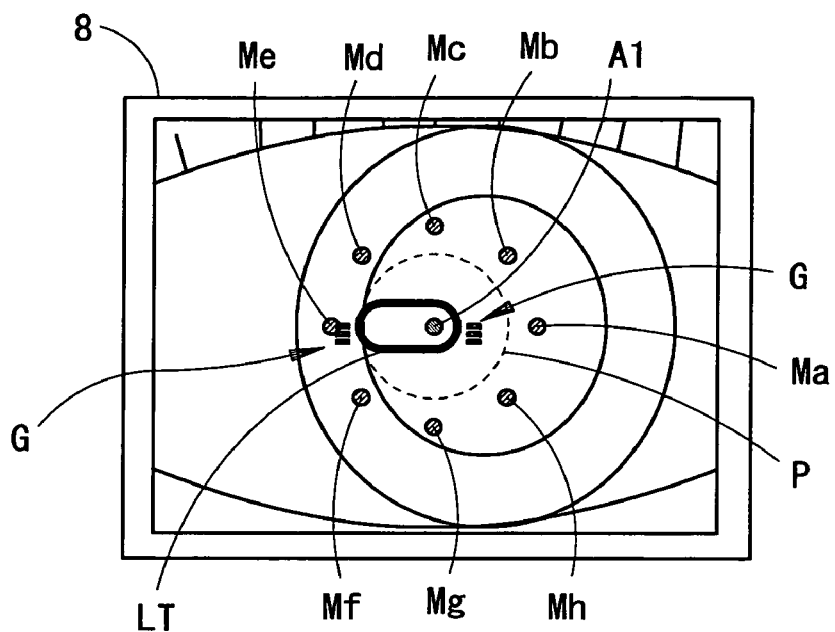
FIGS. 9A and 9B are views showing examples in displaying the anterior-segment observation image at the time of photographing the periphery of the fundus such that the papilla of the right eye is arranged to be the center of the image.

When the alignment mark A1 is positioned in the right part within the reticle mark LT (i.e., the position where the reticle mark LT is displayed at the time of the standard photographing) (see FIG. 7A), the optical axis L1 is brought to a state where the alignment thereof is performed with respect to the vicinity of a corneal vertex Ev of the eye E (see FIG. 8A). When the display is switched to the anterior-segment observation image from the fundus observation image in this state, the image shown in FIG. 9A is displayed. In such an alignment state, the fundus observation image with fewer flares caused by reflection from the cornea or a crystalline lens can be easily obtained since a deviation between the corneal vertex Ev and the optical axis L1 is small. However, the fundus illumination light is apt to be blocked by an iris of the eye E depending on a dilated state of the pupil of the eye E. Besides, the corneal vertex Ev in the preferred embodiment of the present invention indicates a point where a straight line which is parallel to the optical axis L1 and passes through the center of corneal curvature of the eye E intersects the cornea Ec.

Figure 8B:
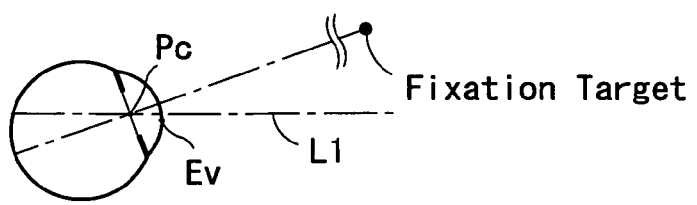
Figure 9B:
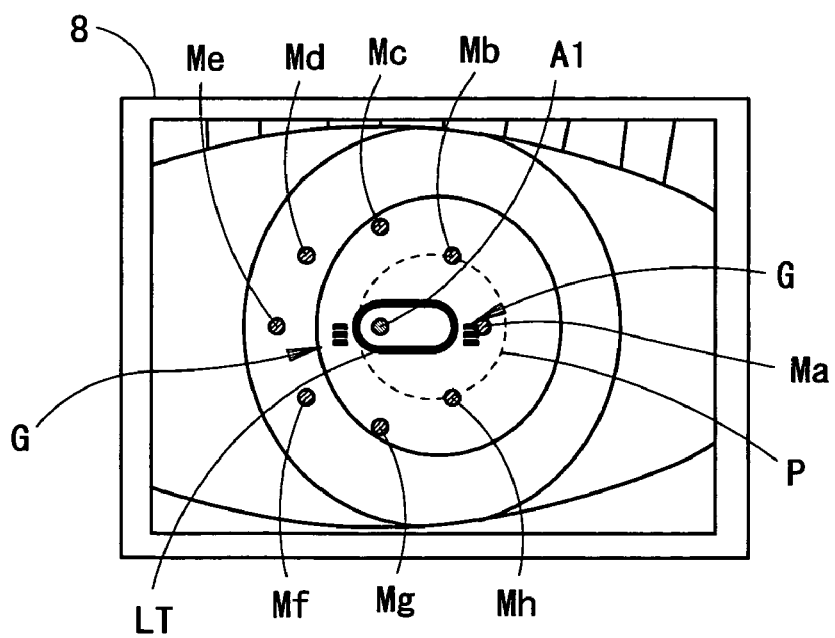

When the alignment mark A1 is positioned in the left part within the reticle mark L1 (see FIG. 7B), the optical axis L1 is brought to a state where the alignment thereof is performed with respect to the vicinity of a pupil center Pc of the eye E (see FIG. 8B). When the display is switched to the anterior-segment observation image from the fundus observation image in this state, the image shown in FIG. 9B is displayed. In such an alignment state, the fundus illumination light is hardly blocked by the iris. However, the fundus observation image is apt to suffer flares since the deviation between the corneal vertex Ev and the optical axis L1 is large.

Figure 8C:
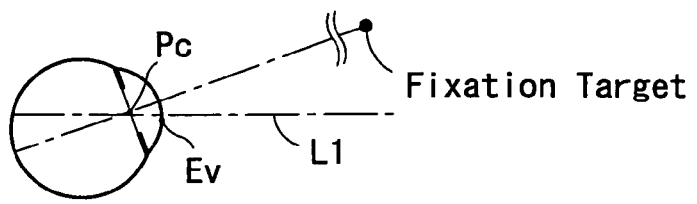

When the alignment mark A1 is positioned in the vicinity of the center within the reticle mark LT (see FIG. 7C), the optical axis L1 is brought to a state where the alignment thereof is performed with respect to the vicinity of the midpoint between the corneal vertex Ev and the pupil center Pc (see FIG. 8C). In such an alignment state, the fundus illumination light is hardly blocked by the iris compared with the case where the alignment of the optical axis L1 is performed with respect to the corneal vertex Ev. In addition, the fundus observation image is less apt to suffer flares compared with the case where the alignment of the optical axis L1 is performed with respect to the pupil center Pc.

When the photographing unit 3 is moved in the X- and Y-directions within a range where the alignment mark A1 is positioned within the reticle mark LT, and a preferable fundus observation image with fewer flares and less unevenness in illumination becomes observable on the screen of the monitor 8, the photographing is performed through operation of the switch 4b (the focusing may be performed again before the photographing). Accordingly, a preferable fundus photographing image with fewer flares and less unevenness in illumination can be easily obtained. That is to say, the optical axis L1 (the photographing unit 3) can be guided to an alignment state where the preferable fundus photographing image can be easily obtained.

In the above description, while the display shape of the reticle mark LT is varied in accordance with the presenting position of the fixation target in a fundus observation state (at the time of displaying the fundus observation image), it is also preferable that the display shape of the reticle mark LT is varied in accordance with the presenting position of the fixation target in an anterior-segment observation state (at the time of displaying the anterior-segment observation image). This allows smooth periphery photographing of the fundus after the switching from the anterior-segment observation state to the fundus observation state.

In the above description, while the fixation target presenting system (fixation target presenting optical system) is provided in the photographing unit 3, it is also preferable that the fixation target presenting system is provided outside the photographing unit 3. As the fixation target presenting system, a known system such as a system using a liquid crystal display and a system using a plurality of fixation target light sources (fixation lamps) can be used. It is essential only that the systems be arranged so that the display shape of the reticle mark LT is varied in accordance with the presenting position of the fixation target.

In the above description, while the alignment mark is electrically formed and displayed in the position on the screen of the monitor corresponding to the center position of the plurality of the alignment target images formed by the alignment target projection optical system, it is also preferable that the picked-up alignment target image is displayed as it is with the fundus observation image and/or the anterior-segment observation image without forming and displaying the alignment mark, and the alignment in the X- and Y-directions is performed based on the displayed images and the reticle mark. In addition, it is also preferable that the alignment target is projected onto the eye from the front, not in a slanting direction.

In the above description, while the camera (the image-pickup element) for picking up the anterior-segment observation image doubles as the alignment target image detection means (i.e., the anterior-segment observation optical system doubles as the alignment target image detection optical system), it is also preferable that a dedicated photodetector that defines the alignment target image detection means (the alignment target image detection optical system) is provided.

In the above description, while the camera (the image-pickup element) for picking up the fundus observation image and the camera (the image-pickup element) for picking up the anterior-segment observation image are separately provided, it is also preferable that the anterior-segment observation image is picked up by the camera (the image-pickup element) for picking up the fundus observation image. In other words, the camera (the image-pickup element) may be shared.

Figure 10A:
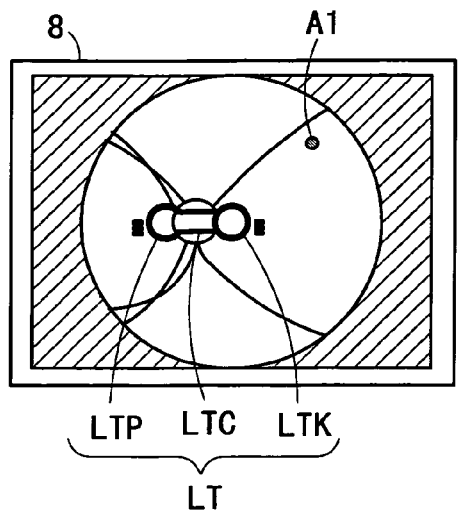
FIGS. 10A, 10B and 10C are views showing modified examples of the display shape of the reticle mark.

The display shape of the reticle mark LT is not limited to the above-described display shape, and it is essential only that the display shape be arranged such that the optical axis L1 is guided within a predetermined region from the vicinity of the corneal vertex to the vicinity of the pupil center. For example, as shown in FIG. 10A, the reticle mark LT may have a display shape including a mark LTK for positioning the optical axis L in the vicinity of the corneal vertex, a mark LTP for positioning the optical axis L1 in the vicinity of the pupil center, and a mark LTC which connects the mark LTK and the mark LTP.

Figure 10B:
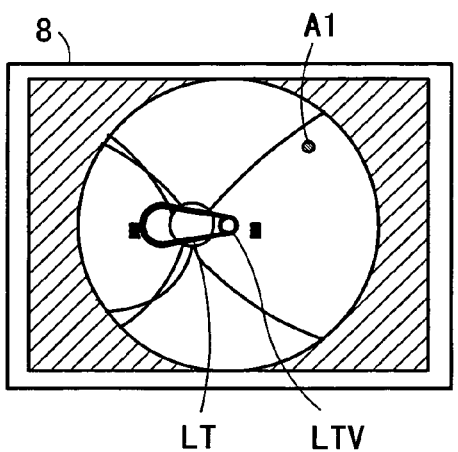
Figure 10C:
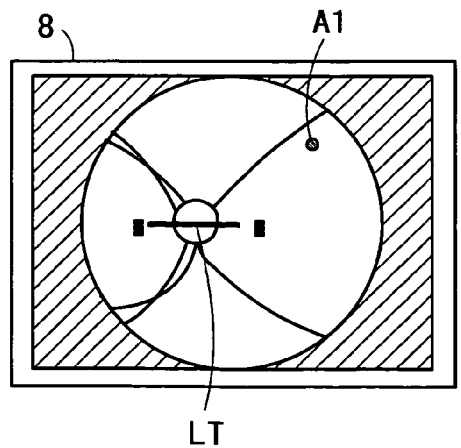

In addition, as shown in FIG. 10B, the reticle mark LT may have the display shape in which a region LTV for positioning the optical axis L1 in the vicinity of the corneal vertex is smaller than a region for positioning the optical axis L1 in the vicinity of the pupil center and other regions. By having such a display shape, the permissible range of the alignment is made larger when the optical axis L1 is positioned in the vicinity of the pupil center where flares are apt to be caused, so that a preferable fundus photographing image with fewer flares can be easily obtained. Meanwhile, the permissible range of the alignment is made smaller when the optical axis L1 is positioned in the vicinity of the corneal vertex where flares are hardly caused, so that a preferable fundus photographing image with fewer flares can be easily obtained. In addition, the reticle mark LT may have the display shape of a line, as shown in FIG. 10C.

The reticle mark LT may be varied in size in accordance with the pupil diameter of the eye E which is obtained based on the image signal from the camera 65. For example, if the pupil diameter of the eye E is larger, the reticle mark LT is made larger, and if the pupil diameter of the eye E is smaller, the reticle mark LT is made smaller.

Accompanied by variation of the display shape of the reticle mark LT, the permissible range of the alignment for making the display switching from the anterior-segment observation image to the fundus observation image may be changed. For example, at the time of periphery photographing, the permissible range of the alignment may be made larger in the direction where the direction of the visual line of the eye E is guided than that at the time of standard photographing.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A fundus camera comprising:
   a photographing optical system having a photographing optical axis, for photographing a fundus of an examinee's eye;
   a fundus observation optical system having an image-pickup element which picks up an observation image of the fundus of the eye;

an alignment target projection optical system for projecting an alignment target onto an anterior segment of the eye;

an alignment target image detection optical system having a photodetector which detects an image of the alignment target;

a photographing unit which houses the photographing optical system, the fundus observation optical system, the alignment target projection optical system and the alignment target image detection optical system;

a moving mechanism which moves the photographing unit in order to perform alignment of the photographing optical axis so as to have a predetermined positional relationship with the eye;

a fixation target presenting system for presenting a fixation target for guiding a direction of a visual line of the eye, a presenting position of the fixation target being arranged to be selectable or changeable;

a display unit; and a controller which controls the display unit to display the fundus observation image and the alignment target image on a screen of the display unit, wherein the controller includes a program for electrically forming and displaying a reticle mark that defines an alignment reference in a predetermined position on the screen at the time of displaying the fundus observation image while varying a display shape of the reticle mark in accordance with the presenting position of the fixation target.

2. The fundus camera according to claim 1, wherein the presenting position of the fixation target is arranged to be selectable or changeable between a position for standard photographing such that a center portion of the fundus is photographed and a position for periphery photographing such that a peripheral portion of the fundus is photographed, and the program is arranged to display a reticle mark for standard photographing in response to selection of or change to the position for standard photographing, and display a reticle mark for periphery photographing having a display shape which is made larger in a direction where the direction of the visual line of the eye E is guided than a display shape of the reticle mark for standard photographing in response to selection of or change to the position for periphery photographing.

3. The fundus camera according to claim 1, wherein the presenting position of the fixation target is arranged to be selectable or changeable between a position for standard photographing such that a center portion of the fundus is photographed and a position for periphery photographing such that a peripheral portion of the fundus is photographed, and the program is arranged to vary the display shape of the reticle mark so that the photographing optical axis is positioned within a predetermined region from a vicinity of a corneal vertex to a vicinity of a pupil center when the alignment target image is positioned within the reticle mark in response to selection of or change to the position for periphery photographing.

4. The fundus camera according to claim 1, wherein the presenting position of the fixation target is arranged to be selectable or changeable between a position for standard photographing such that a center portion of the fundus is photographed and a position for periphery photographing such that a peripheral portion of the fundus is photographed, and the program is arranged to vary the display shape of the reticle mark based on a virtual line between a display position of the alignment target image at the time when the alignment of the photographing optical axis is performed with respect to a vicinity of a corneal vertex and a display position of the alignment target image at the time when the alignment of the photographing optical axis is performed with respect to a vicinity of a pupil center in response to selection of or change to the position for periphery photographing.

5. The fundus camera according to claim 4, wherein the program is arranged to vary the reticle mark to have the display shape of one of a frame which surrounds the virtual line and a line which traces the virtual line.

6. The fundus camera according to claim 1, wherein the program is arranged to electrically form and display an alignment mark, instead of the alignment target image, of which a relative distance from the reticle mark varies in accordance with an alignment deviation amount of the photographing optical axis with respect to the eye which is obtained based on an output signal from the photodetector.

7. The fundus camera according to claim 1, further comprising:

an anterior-segment observation optical system having an image-pickup element which picks up an observation image of the anterior segment of the eye, wherein the controller controls the display unit to display the anterior-segment observation image and the alignment target image on the screen of the display unit, and the program is arranged to electrically form and display the reticle mark in the predetermined position on the screen at the time of displaying the anterior-segment observation image while varying the display shape of the reticle mark in accordance with the presenting position of the fixation target.

8. A fundus camera comprising:

a photographing optical system having a photographing optical axis, for photographing a fundus of an examinee's eye;

a fundus observation optical system having a first image-pickup element which picks up an observation image of the fundus of the eye;

an alignment target projection optical system for projecting an alignment target onto an anterior segment of the eye;

an anterior-segment observation optical system having a second image-pickup element which picks up an observation image of the anterior segment of the eye and an image of the alignment target;

a photographing unit which houses the photographing optical system, the fundus observation optical system, the alignment target projection optical system and the anterior-segment observation optical system;

a moving mechanism which moves the photographing unit in order to perform alignment of the photographing optical axis so as to have a predetermined positional relationship with the eye;

a fixation target presenting system for presenting a fixation target for guiding a direction of a visual line of the eye, a presenting position of the fixation target being arranged to be selectable or changeable, a display unit; and a controller which controls the display unit to switch display on a screen of the display unit between the fundus observation image and the alignment target image, and the anterior-segment observation image and the alignment target image, wherein the controller includes a program for electrically forming and displaying a reticle mark that defines an alignment reference in a predetermined position on the screen at least one of at the time of displaying the fundus observation image and at the time of displaying the anterior-segment observation image while varying a display shape of the reticle mark in accordance with the presenting position of the fixation target.

9. The fundus camera according to claim 8, wherein the program is arranged to electrically form and display an alignment mark, instead of the alignment target image, of which a relative distance from the reticle mark varies in accordance with an alignment deviation amount of the photographing optical axis with respect to the eye obtained based on an output signal from the second image-pickup element.

* * * * *